US00PP34093P2

(12) United States Plant Patent
Yencho et al.

(10) Patent No.: US PP34,093 P2
(45) Date of Patent: Apr. 5, 2022

(54) SWEETPOTATO PLANT NAMED 'NCPUR13-0315'

(50) Latin Name: ***Ipomoea batatas* (L.)**
Varietal Denomination: NCPUR13-0315

(71) Applicant: North Carolina State University, Raleigh, NC (US)

(72) Inventors: George Craig Yencho, Raleigh, NC (US); Kenneth Vincent Pecota, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 17/300,480

(22) Filed: Jul. 15, 2021

(51) Int. Cl.
*A01H 5/06* (2018.01)
*A01H 6/00* (2018.01)

(52) U.S. Cl.
USPC ..... Plt./258
CPC ..... *A01H 6/00* (2018.05)

(58) Field of Classification Search
USPC ..... Plt./258
CPC ..... A01H 5/06; A01H 5/12
See application file for complete search history.

*Primary Examiner* — Kent L Bell
(74) *Attorney, Agent, or Firm* — Myers Bigel, P.A.

(57) ABSTRACT

*Ipomoea batatas* 'NCPUR13-0315' is a purple fleshed, smooth skinned, dark purple-colored, table stock sweetpotato. 'NCPUR13-0315' has good yields of well-shaped and uniformly sized No.1 sized roots. It is a mid-season cultivar for optimal production of No.1 sized roots.

8 Drawing Sheets

Latin name of the genus and species: The Latin name of the novel plant cultivar disclosed herein is *Ipomoea batatas* (L.) Lam.

Variety denomination: This new and distinct sweetpotato cultivar of *Ipomoea batatas* (L.) Lam. has been given the denomination 'NCPUR13-0315'.

BACKGROUND OF THE INVENTION

*Ipomoea batatas* is a member of the morning glory family Convolvulaceae. This species is grown worldwide, and it exhibits a wide range of plant forms and colors. Grown by farmers worldwide, the cultivated members of *Ipomoea batatas* are commonly produced for consumption of their nutritious, enlarged storage roots. This contrasts with potatoes (*Solanum tuberosum*) that produce an edible tuber derived from an underground stem, which is similar in structure to above ground stems.

Purple fleshed sweetpotatoes are a small percentage of the US market with there being two distinct types. The first type is white skinned and purple fleshed with the main cultivar in this group being the heirloom cultivar 'Okinawa' (not patented), which is grown in Hawaii for the U.S. market. This heirloom cultivar is very poorly adapted to the growing regions on the mainland including NC, CA, LA and MS. The second type is purple skinned and purple fleshed. There are a few cultivars of this second type grown in the U.S., mainly 'Mokuau' aka 'Molokai Purple' (not patented), which is grown in Hawaii, and 'Stokes Purple' (U.S. Plant Pat. No. 17,976), which is grown on the U.S. mainland. Several different names have been used for these and other similar varieties, some of which have been previously introduced from Southeast Asia via various methods. However, none of these are particularly well adapted to NC growing conditions. 'NCPUR06-0020' (U.S. Plant Pat. No. 25,538) was developed and released for its high pigment value for industrial use, but its eating quality is poor.

'NCPUR13-0315' provides an improvement over 'Stokes Purple' and other purple-skinned, purple-fleshed cultivars known to the inventors for table stock use in terms of its adaptability, yield, and marketable shapes.

Lineage. 'NCPUR13-0315' originated from a paired cross between 'NCP06-0016', the female parent, and 'NC08-0553', the male parent, in Raleigh, N.C. Both parents are non-patented lines from the breeding program. Plants were crossed from October 2011 to April 2012 with seed from the same cross combined across the crossing dates.

Seedlings from the 2012 purple polycross nursery were planted in greenhouses in Clinton, N.C. in March of 2013. A single cutting was taken from each seedling and planted in the field on May 23, 2013 in Kinston N.C. and 'NCPUR13-0315' was selected as a "single plant selection" on Aug. 27, 2013. This "single plant selection" included all of the storage roots derived from the single plant cutting planted on May 23$^{rd}$, with 2-10 storage roots being saved over the winter in our storage facility in Clinton, N.C. for propagation the next year via vegetive propagation in the same location.

Asexual Reproduction. The first asexual reproduction of 'NCPUR13-0315' occurred in Clinton, N.C. 'NCPUR13-0315' has been propagated as vegetative stem cuttings and/or storage root derived stem cuttings derived from adventitious sprouts emanating from its storage roots since its original selection in August of 2013 in Kinston, N.C. After further cycles of selection for horticultural traits and disease screenings, 'NCPUR13-0315' was subjected to meristem tip culture and subsequent tissue culture maintenance to eliminate viruses and pathogens via meristem tip culture. The characteristics disclosed herein for 'NCPUR13-0315' have remained stable and the plant has reproduced true to type through successive generations of asexual propagation.

SUMMARY OF THE INVENTION

'NCPUR13-0315' is a purple-fleshed, dark purple skin colored table stock sweetpotato. The storage roots of 'NCPUR13-0315' tend to be blocky to round elliptic; longer than 'Covington' (U.S. Plant Pat. No. 18,516) and shorter than 'Stokes Purple', and more uniform in size and shape than 'Stokes Purple'. Marketable yields of 'NCPUR13-0315' are similar to 'Covington' and higher than 'Stokes Purple', the main orange and purple fleshed sweetpotato cultivars produced in the US, respectively. Plants from sprouted roots are ready about a week before 'Covington', and a week or two later than 'Stokes Purple'. The anthocyanin content averages about twice as much as 'Stokes Purple'. The flavor of baked storage roots of 'NCPUR13-0315' have been judged to be good by standardized and informal taste panels, similar to 'Stokes Purple', the main cultivar of this type.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*.

DETAILED BOTANICAL DESCRIPTION

The following is a detailed description of the botanical characteristics of a new and distinct cultivar of *Ipomoea batatas* plant given the designation 'NCPUR13-0315'. All colors cited herein refer to The Royal Horticulture Society Colour Chart designations (The Royal Horticultural Society, London, 1995, $4^{th}$ ed.) except where general terms of ordinary dictionary significance are used. Plant descriptions are based on the standardized international sweetpotato descriptors established jointly by the International Potato Center (CIP), Lima, Peru; The Asian Vegetable Research and Development Center (AVRDC), Taipei, Taiwan; and the International Board for Plant Genetics Resources (IBPGR), Rome, Italy (CIP, AVRDC, IBPGR. 1991. Descriptors for Sweet Potato. Huaman, Z., editor. International Board for Plant Genetic Resources, Rome, Italy, 134pp.). Where dimensions, sizes, colors, and other characteristics are given, it is to be understood that such characteristics are approximations or averages set forth as accurately as practicable.

The descriptions and measurements of plant canopy reported herein were done on field grown plants 57 days after planting (DAP). The plants were grown in Kinston, N.C. under common commercial sweetpotato production practices during June through October. 'NCPUR13-0315' has not been observed under all possible environmental conditions; therefore, the phenotype may vary under different environmental conditions such as season, temperature, light intensity, day length, cultural conditions, and the like, without however, any variance in the genotype.

The following discussion provides a description of the new *Ipomoea batatas* 'NCPUR13-0315' with 'Stokes Purple' and 'NCPUR06-0020' for comparison. The parent lines 'NC06-0016' and 'NC08-0553' were no longer propagated at the time when 'NCPUR13-0315' was being evaluated, so they were not used for comparison. Neither of the parent lines are grown commercially.

Classification.

*Botanical name.*—*Ipomoea batatas* (L.) Lam.

*Common name.*—Sweetpotato.

*Variety name.*—'NCPUR13-0315'.

Figure 1:
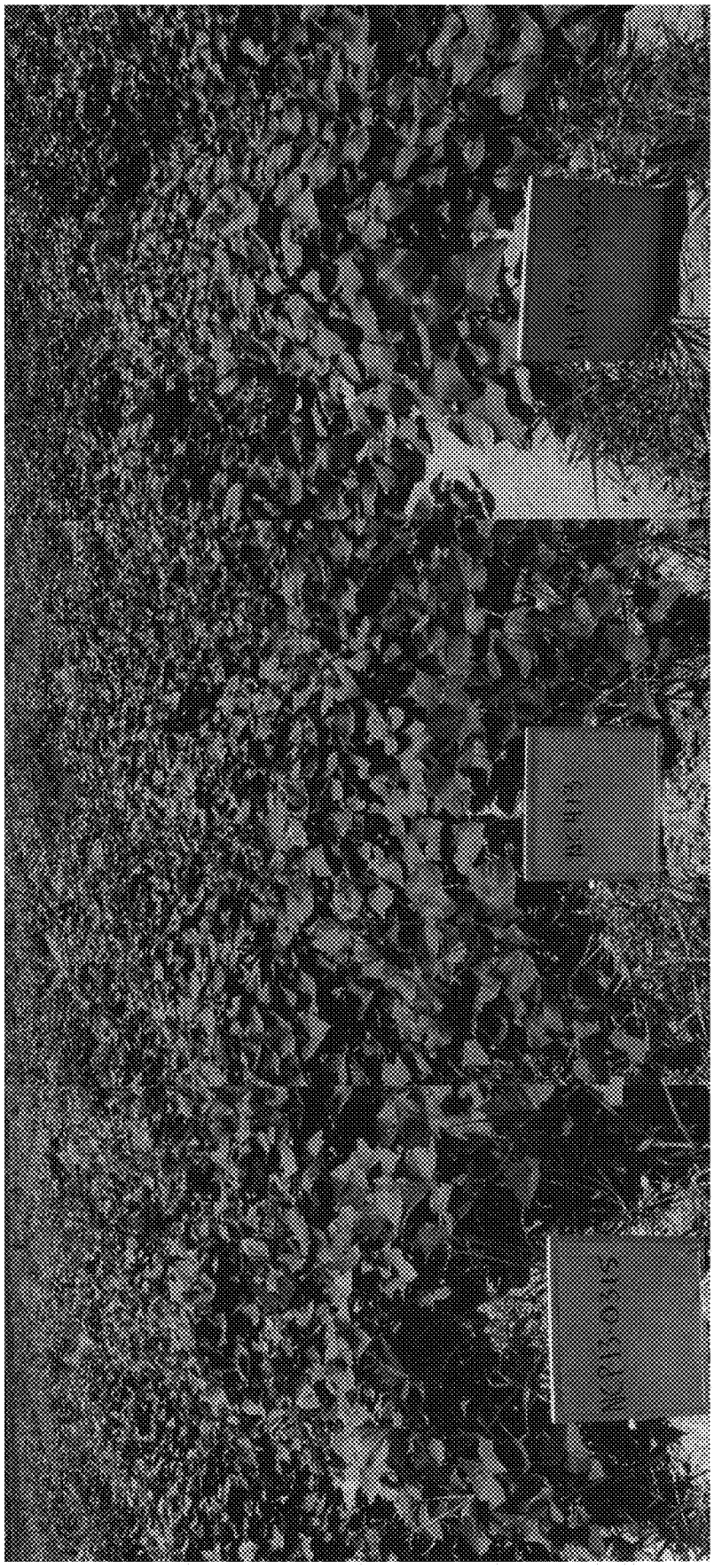
FIG. 1 is a color photograph of the above ground plant canopy produced by the new cultivar 'NCPUR13-0315' (abbreviated as NCP13-0315) (left panel), 'Stokes Purple' ('NC413') (middle panel) and 'NCPUR06-0020' (abbreviated as NCP06-0020) (right panel) 57 days after planting at in Kinston, N.C. in 2017.

Growth conditions whole-plant canopy structure: FIG. 1 is a color photograph of the canopy biomass produced by the new cultivar 'NCPUR13-0315' and contrasted with 'Stokes Purple', and 'NCPUR06-0020'. Measurements were collected on field-grown plants at 57 DAP using 20 measurements per trait and recorded as the mean±standard deviation. Measurements of key features are presented in Table 1.

Figure 2A:
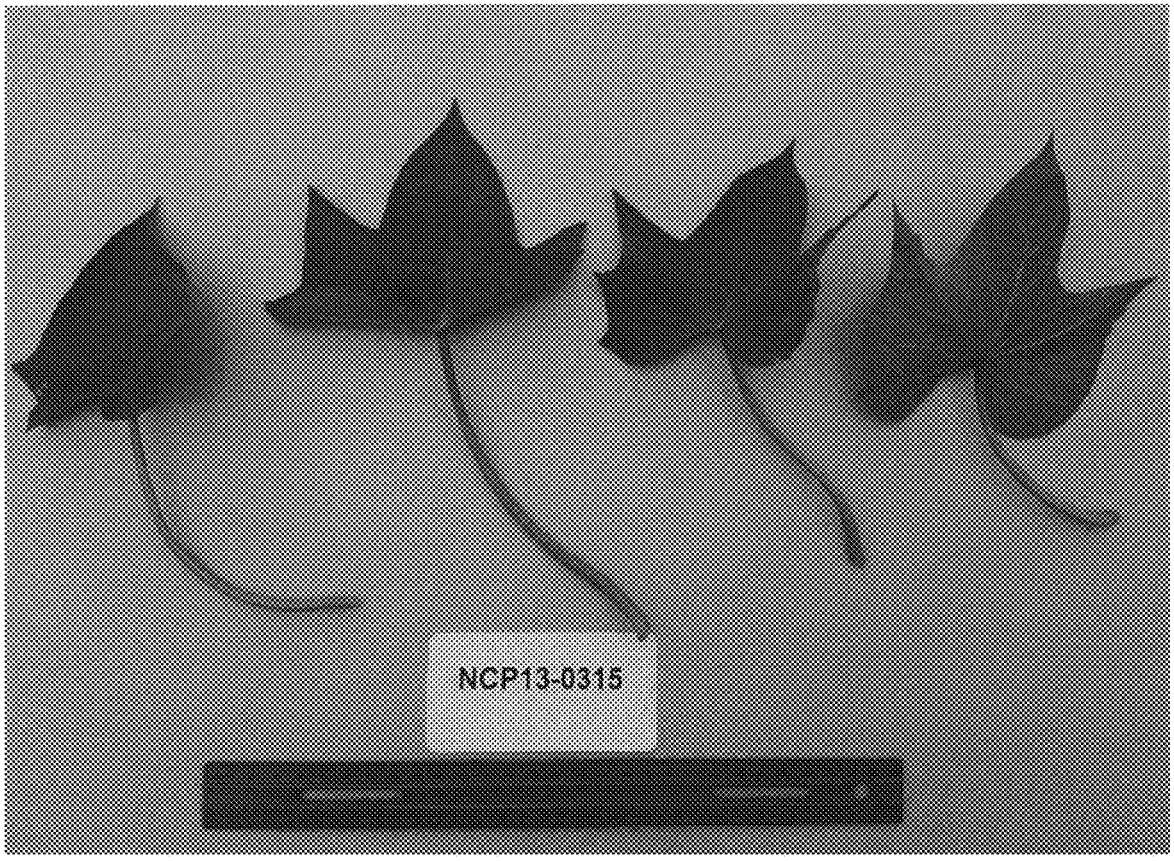
FIGS. 2A-2C are color photographs of typical mature leaves of 'NCPUR13-0315' (abbreviated as 'NCP13-0315') (FIG. 2A), 'Stokes Purple' ('NC413') (FIG. 2B), and 'NCPUR06-0020' (abbreviated as 'NCP06-0020') (FIG. 2C), 57 days after planting in Kinston, N.C. in 2017.
Figure 2B:
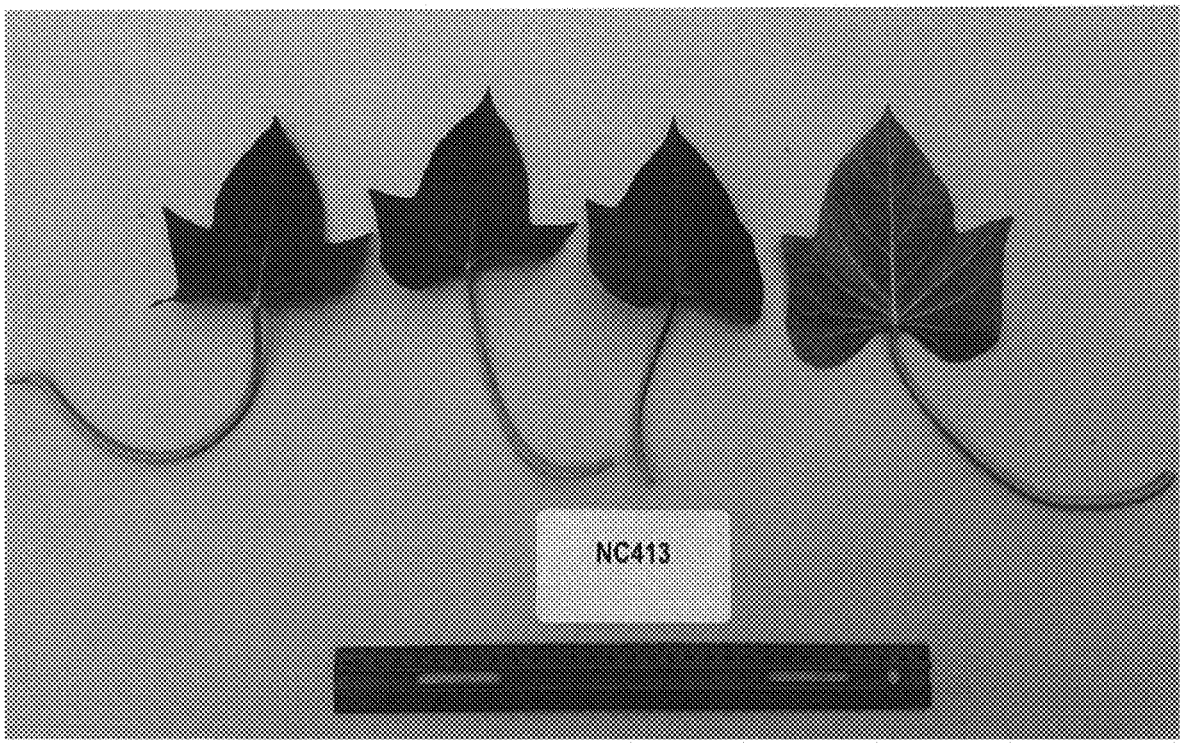
Figure 2C:
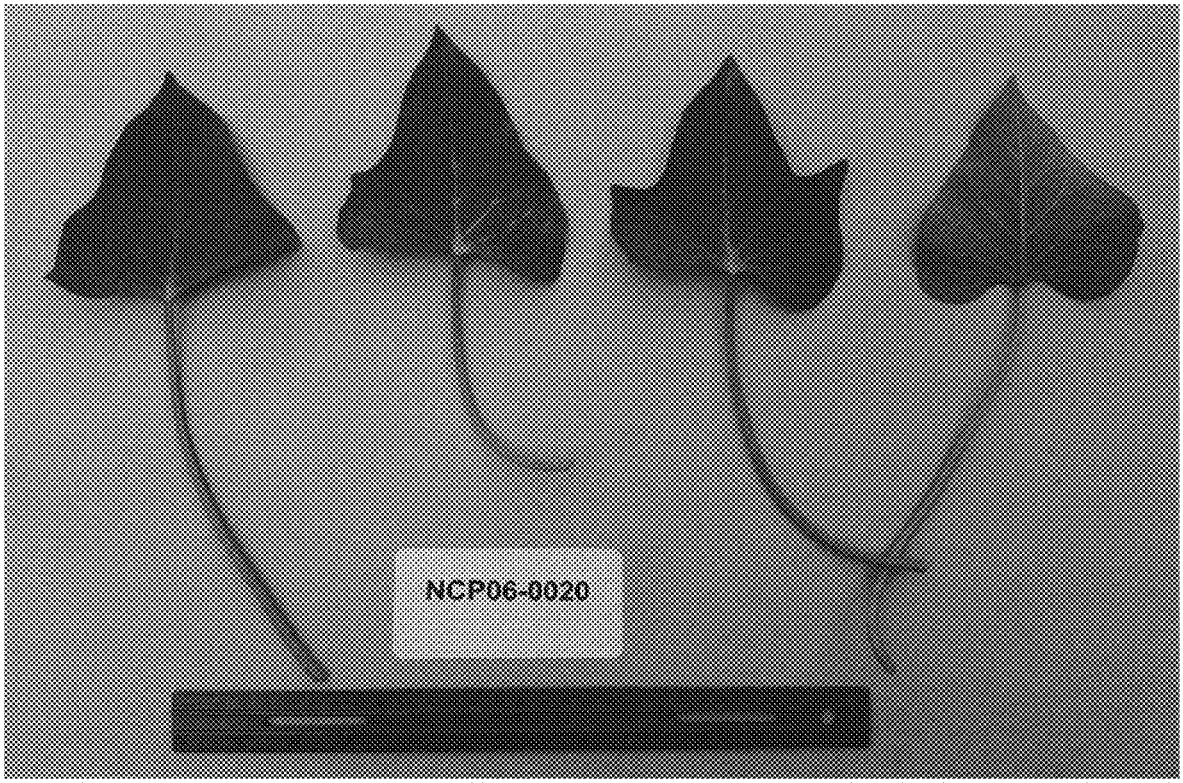
Figure 3A:
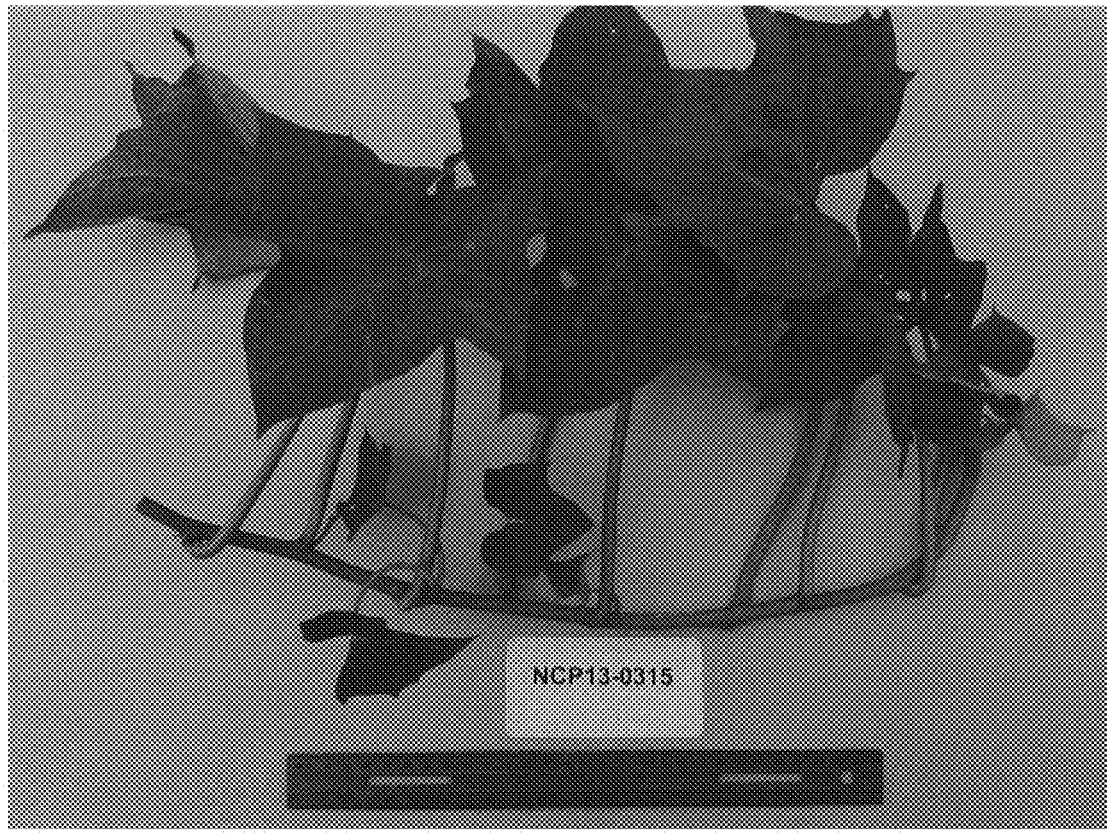
FIGS. 3A-3C are color photographs showing typical vines and the variety of leaves of 'NCPUR13-0315' (abbreviated as 'NCP13-0315') (FIG. 3A), 'Stokes Purple' ('NC413') (FIG. 3B) and 'NCPUR06-0020' (abbreviated as 'NCP06-0020') (FIG. 3C), 57 days after planting in Kinston N.C. in 2017.
Figure 3B:
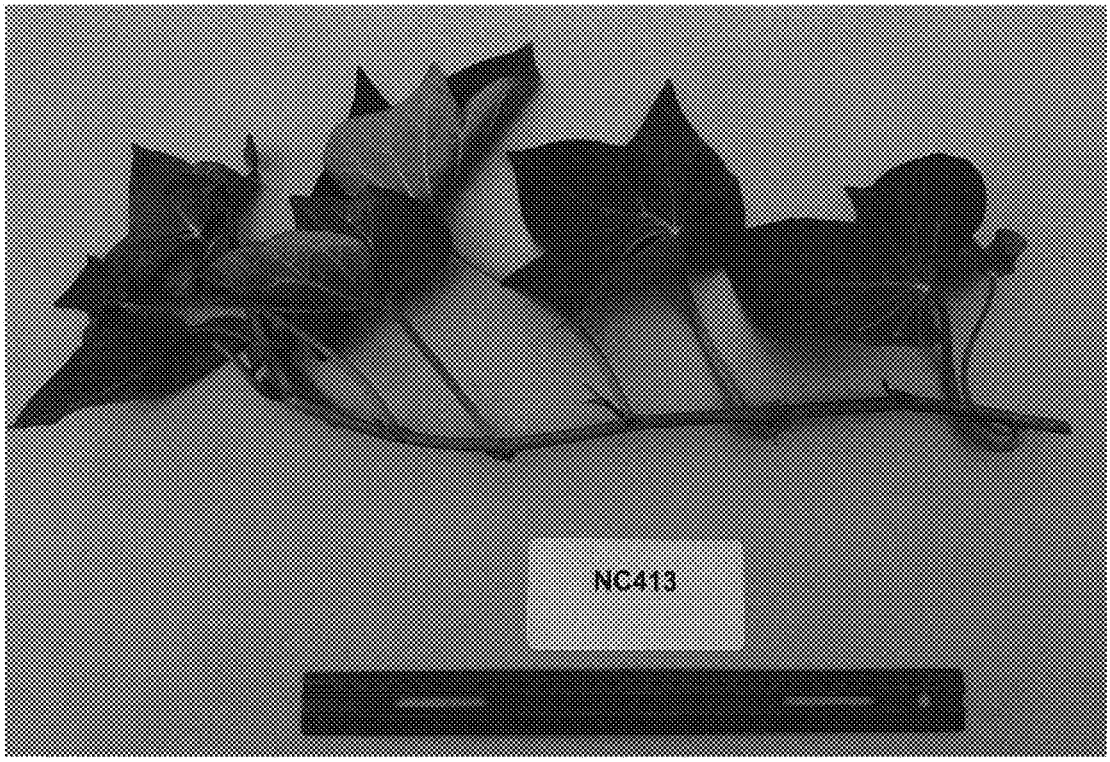
Figure 3C:
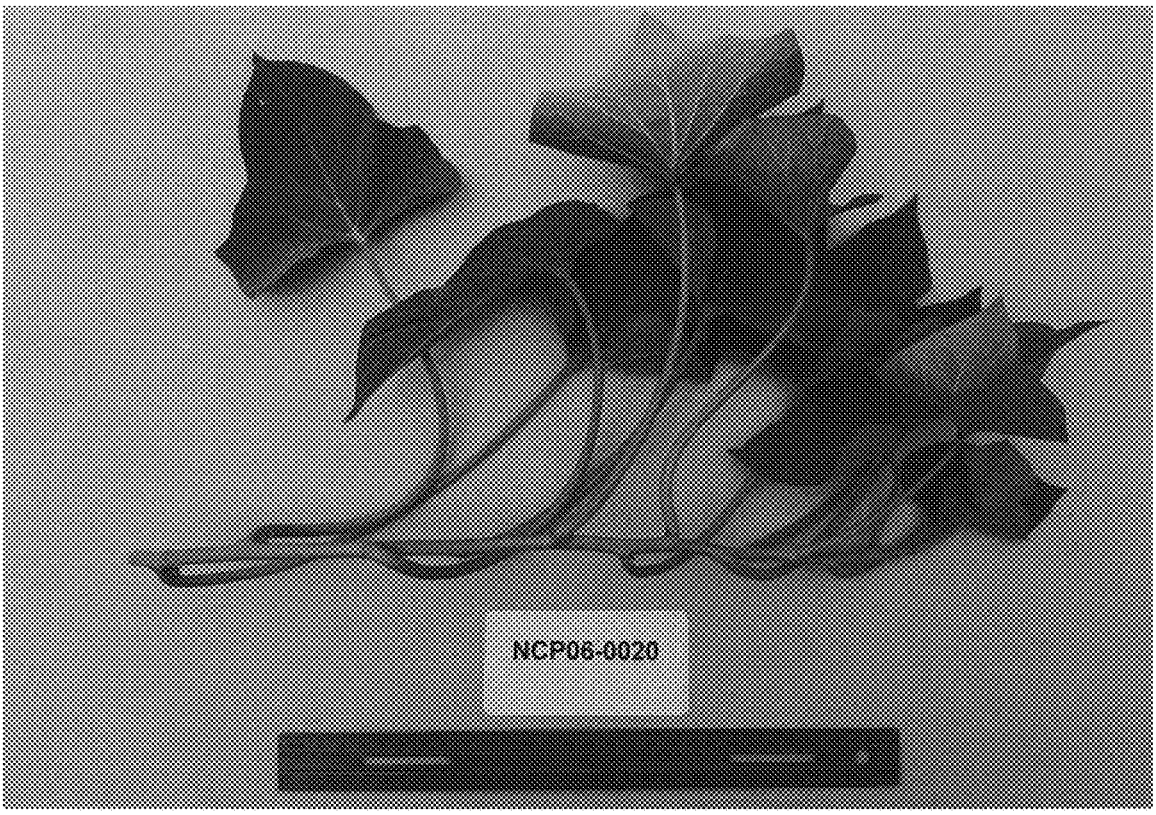

Foliage: The leaves of 'NCPUR13-0315' are alternate and simple in structure, and cordate to lobed in shape with 1-3 teeth to slight lobing and 0-3 lobes. (see FIGS. 2A and 3A). The leaves have a smooth texture and matte finish. The shape of the central lobe is triangular. Stem tip anthocyanin coloration is absent and stem tip pubescence is absent. A detailed description of leaf traits is provided in Table 1. A typical inflorescence of 'NCPUR13-0315' has one cluster of 7.6±1.8 flowers per peduncle. Peduncles are green (144A), averaging 16.5±3.3 cm long and about 2.9±0.3 mm in diameter. Flowers are 4.6±0.5 cm long from the base of the calyx, and the corolla 4.0±0.2 cm wide. Petals are fused to form a rounded limb with smooth edges. The inner throat color is purple (N81A) with a light purple (76C) inner and outer limb. Upper and lower flower texture is smooth. The five sepals making up the calyx are ovate with an acuminate tip. The three inner sepals are 11±0.0 mm long and 6.2±0.6 mm wide while the outer two sepals are shorter, 8.0±0.0 mm long and 2.6±0.2 mm wide. All sepals are green (144A) with smooth edges. The stigmata average 14.4±1 mm in length and are white and the stigma is inserted. Anthers are white with the style white with purple at the base (76C). No fragrance is present.

TABLE 1

Descriptive traits for 'NCPUR13-0030', 'Stokes Purple' and 'NCPUR06-0020' measured on field plants 57 days after planting in Kinston NC in 2017. Numerical measurements are averages of 20 values with standard deviation.

| Clone | Units | 'NCPUR13-0315' | 'Stokes Purple' ('NC413') | 'NCPUR06-0020' |
|---|---|---|---|---|
| #Main vines | | 1.7 ± 0.6 | 1.4 ± 0.5 | 1.6 ± 0.5 |
| Main vine length | cm | 125 ± 27 | 150 ± 27 | 95 ± 29 |
| Main vine diameter at base | mm | 7.3 ± 1.3 | 7.1 ± 1.8 | 7.0 ± 2.1 |
| Main vine diameter at 50 cm from base | mm | 6.1 ± 0.6 | 4.7 ± 0.7 | 5.0 ± 0.8 |
| Number of lateral branches on main vine | | 5.9 ± 1.8 | 5.5 ± 2.2 | 5.5 ± 1.8 |

TABLE 1-continued

Descriptive traits for 'NCPUR13-0030', 'Stokes Purple' and 'NCPUR06-0020' measured on field plants 57 days after planting in Kinston NC in 2017. Numerical measurements are averages of 20 values with standard deviation.

| Clone | Units | 'NCPUR13-0315' | 'Stokes Purple' ('NC413') | 'NCPUR06-0020' |
|---|---|---|---|---|
| Predominant vine color | | green 144B to 144C | green 144B | green 144A to 144B |
| Secondary vine color | | purple nodes N79A | green with few purple spots N79A | none |
| First fully expanded internode length | cm | 4.1 ± 0.9 | 5.0 ± 0.8 | 4.0 ± 1.2 |
| Mature leaf color; upper surface | | green, 147A | green, 147A | green, between 147A and 147B |
| Mature leaf color; lower surface | | green, 146B | green, 147B | green, between 147B and 147C |
| Mature leaf venation | | green, 146B to 146C | green, 146B to C | purple spot in the base of the main rib, N79B |
| Young leaf color: upper surface | | green, 146A to 146B | green (146B to146C) with slight purple (N79A) margins | green, 146B |
| Young leaf color: lower surface | | green, 146B to 146C | green (146B to 146C) with slight purple (N79A) margins | green, 146D |
| Mature Leaf length | cm | 10.8 ± 1.1 | 11.0 ± 0.9 | 11.9 ± 1.2 |
| Mature leaf width | cm | 13.8 ± 1.4 | 13.5 ± 1.7 | 11.1 ± 0.8 |
| Mature leaf shape; general outline | | lobed | lobed | triangular to slightly lobed |
| Mature leaf shape; lobing | | slight to moderate | very slight to slight | very slight to moderate |
| Mature leaf shape; number of lobes | | 0-5 | 0-3 | 0-3 |
| Petiole color: primary | | green with purple near stem 144A and 144B | green 144B to 144C | green 144B |
| Petiole color: seconday | | N79A | none | none |
| Petiole length | cm | 17 ± 2.7 | 17.1 ± 1.7 | 21.4 ± 2.4 |
| Petiole diameter | mm | 5.9 ± 1.1 | 5.2 ± 0.7 | 5.2 ± 0.7 |
| Storage root skin color | | purple, N186C to N77A | purple, N79B to N79C | purple, N77A to N79B |
| Storage root flesh color | | 61A to 71A | purple, 71A | N79B |

Figure 4A:
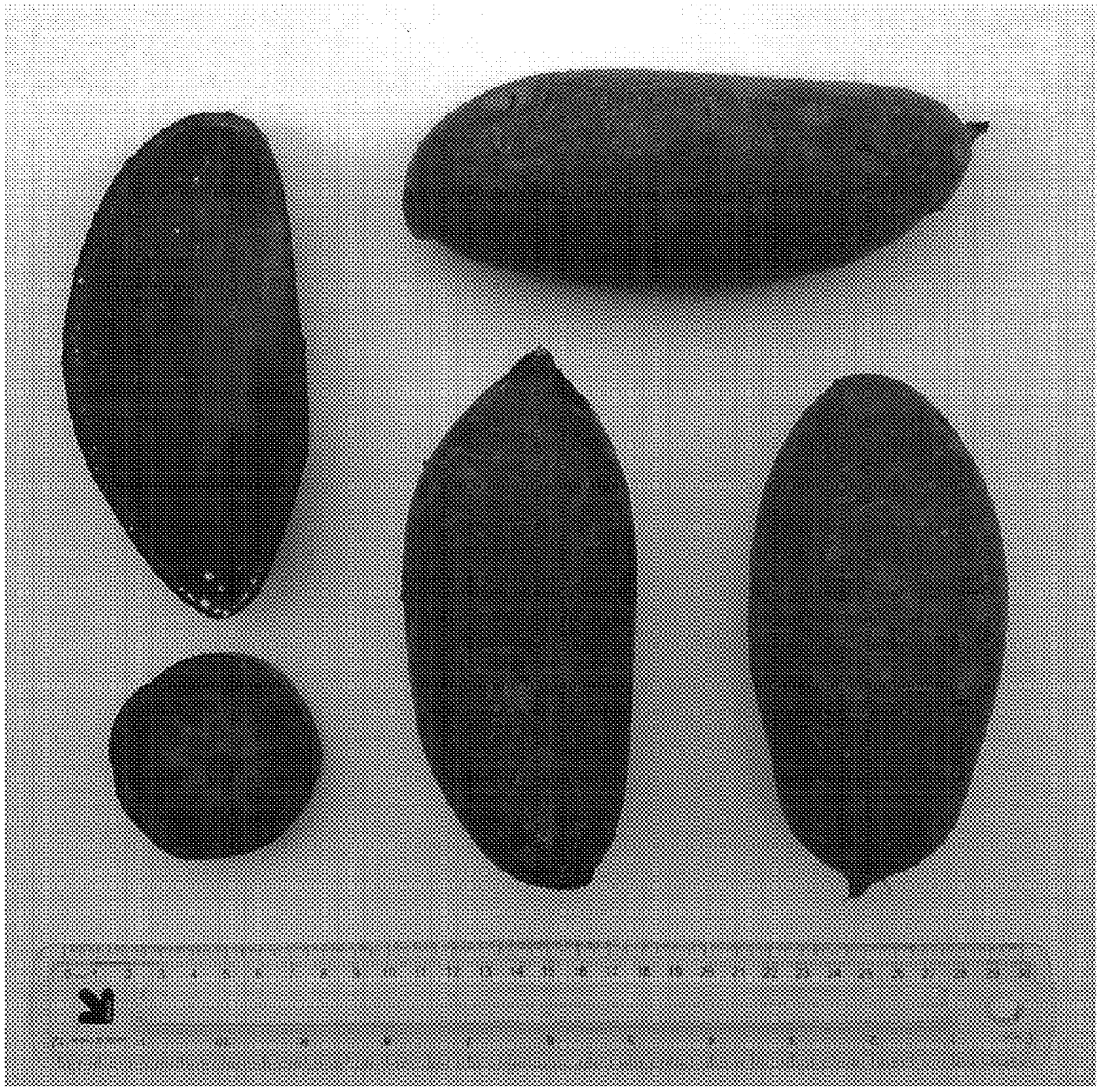
FIGS. 4A-4C are color photographs showing typical storage roots produced by 'NCPUR13-0315' (FIG. 4A), 'Stokes Purple' ('NC413') (FIG. 4B) and 'NCPUR06-0020' (FIG. 4C). The photographs were taken of storage roots that had been stored in a sweetpotato storage facility for approximately three months after harvest.
Figure 4B:
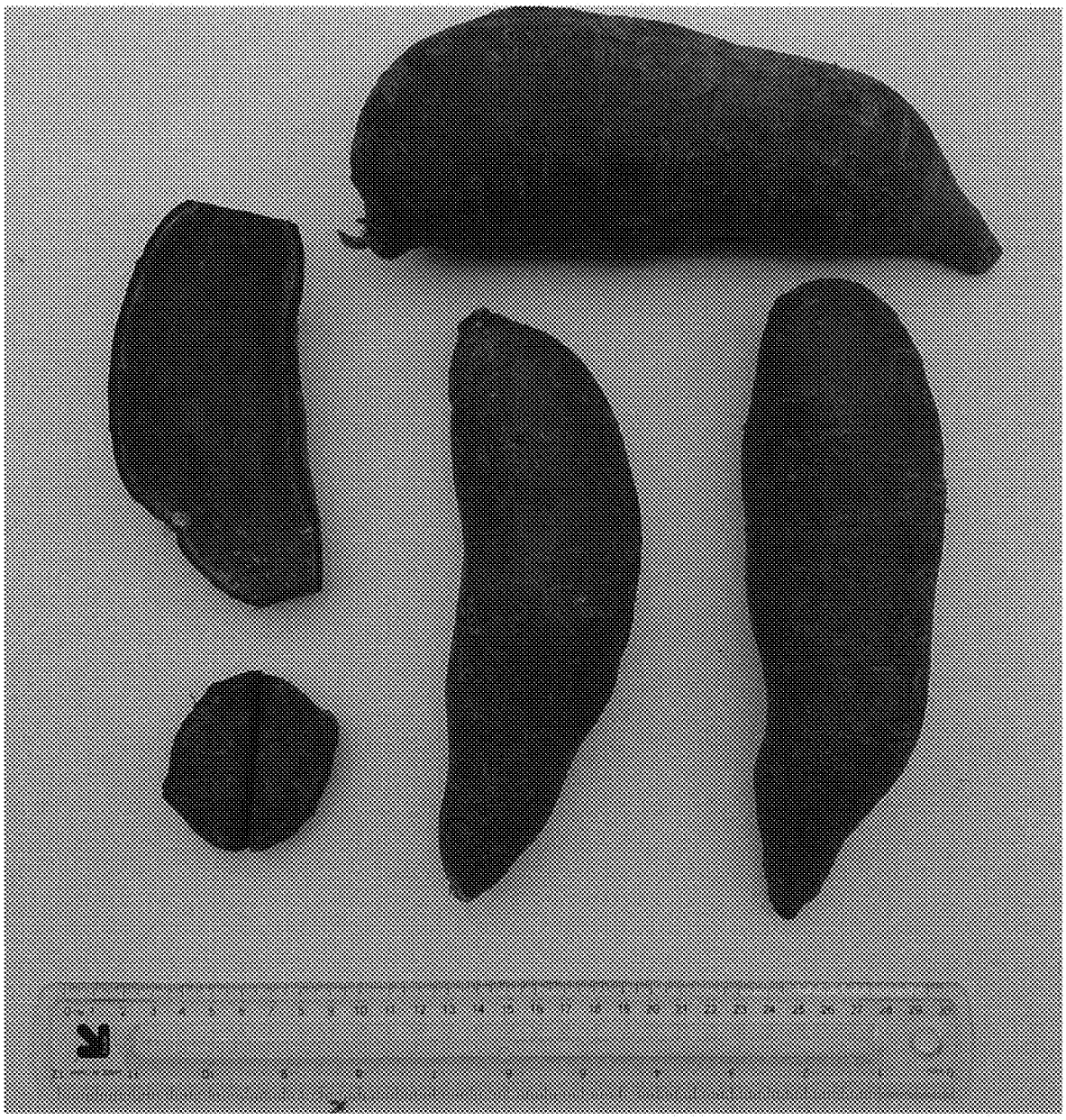
Figure 4C:
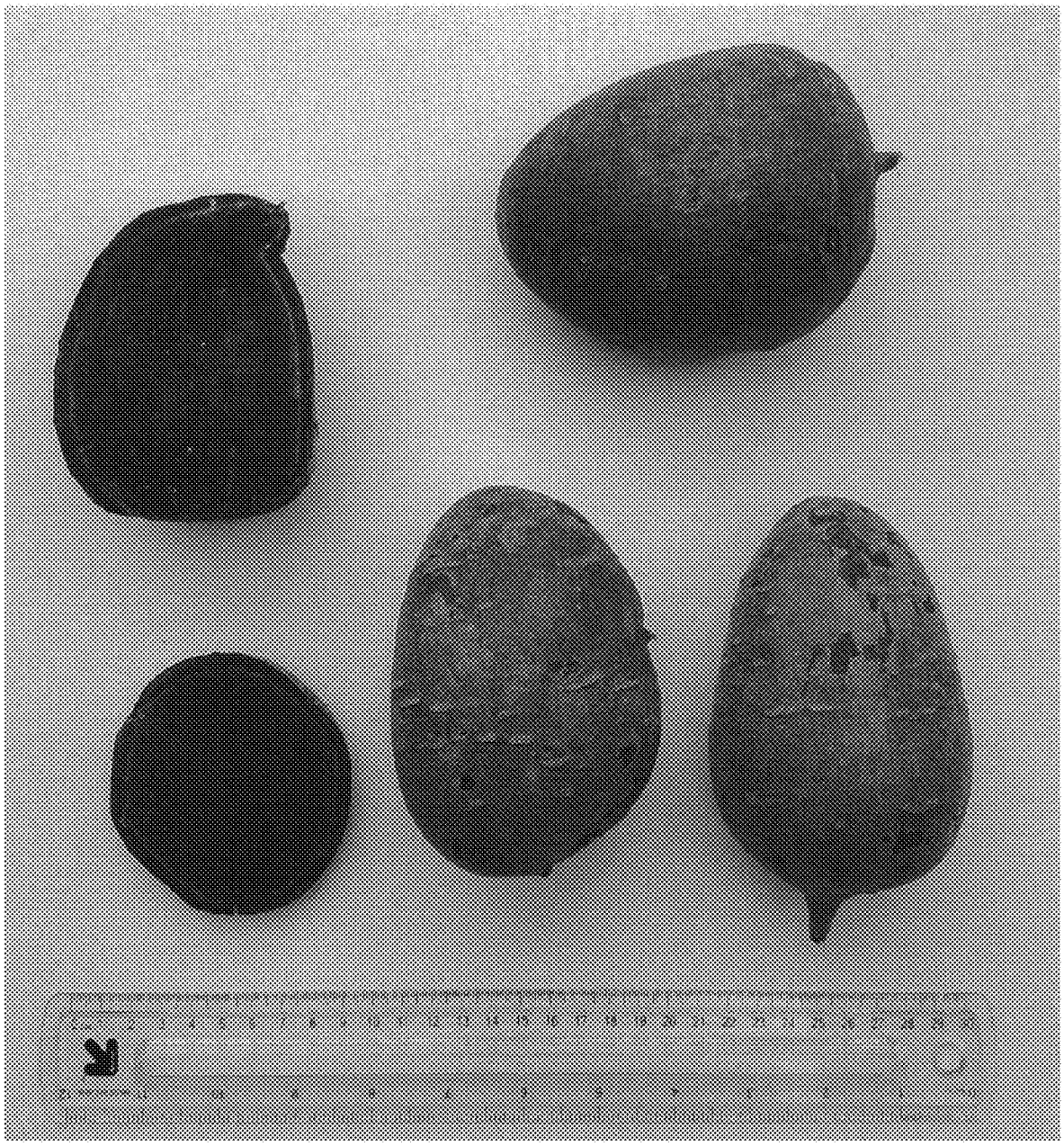

Storage roots: 'NCPUR13-0315' produces purple-fleshed (61A to 71A), smooth skinned, storage roots that are generally blocky to round elliptic. The skin color of 'NCPUR13-0315' is dark purple (N186C to N77A) (FIG. 4A). One of the more desirable attributes of 'NCPUR13-0315' is that it produces uniformly shaped roots with a high percentage of number 1 grade sized roots. Length to diameter ratios of storage roots in 9 trials over four years averaged 2.5, 3.2 and 2.3 for 'NCPUR13-0315', 'Stokes Purple' and 'NCPUR06-0020', respectively. Root number was measured for seven trials in 2017-2019 with 'NCPUR13-0315' averaging 4.4 roots per plant, while 'Stokes Purple' and 'NCPUR06-0020' averaged 2.6 and 4.7 roots per plant, respectively. Carbohydrate profiles, anthocyanin and asparagine levels are presented in Table 2. All three of these cultivars have moderate starch levels, with anthocyanin levels being greater in 'NCPUR06-0020'. The flavor of the baked storage roots of 'NCPUR13-0315' have been judged to be good by standardized and informal taste panels comparing similarly with 'Stokes Purple'.

TABLE 2

Select chemistry of storage roots of 'NCPUR13-0315', 'NCPUR06-0020' and 'Stokes Purple' from trials from 2014 to 2018, samples measured 6-10 weeks after harvest.

| Clone | n | % DM | Fructose g/100 g fresh wt | Glucose g/100 g fresh wt | Sucrose g/100 g fresh wt |
|---|---|---|---|---|---|
| 'NCPUR13-0315' | 22 | 24.1 ± 2.0 | 0.64 ± .10 | 0.88 ± .15 | 1.31 ± .44 |
| 'NCPUR06-0020' | 51 | 27.8 ± 1.8 | 0.34 ± .06 | 0.44 ± .08 | 0.87 ± .20 |
| 'Stokes Purple' | 39 | 28.2 ± 1.7 | 0.31 ± .04 | 0.36 ± .06 | 1.07 ± .21 |

| Clone | n | Starch g/100 g fresh wt | Asparagine mg/g fresh wt | TMA mg/g dry wt |
|---|---|---|---|---|
| 'NCPUR13-0315' | 22 | 46.1 ± 3.8 | 0.86 ± .50 | 3.02 ± .73 |
| 'NCPUR06-0020' | 51 | 51.9 ± 5.6 | 0.73 ± .37 | 3.55 ± .94 |
| 'Stokes Purple' | 39 | 57.3 ± 4.1 | 0.913 ± .50 | 1.42 ± .68 |

Values are based on predictions using Near Infrared Reflectance Spectroscopy (NIRS) calibrations.
Means ± std dev.
TMA total monomeric anthocyanins Storage root yield: Yield comparisons of 'NCPUR13-0315' are with 'Stokes Purple' ('NC413') the most common purple grown in NC and 'Covington', the major orange fleshed sweetpotato cultivar grown in North Carolina (Table 3). 'NCPUR06-0020' is not used in trials for table stock use and was not in these trials. In the 9 replicated yield trials, 'NCPUR13-0315' averaged 189% of the total marketable yield (TMY) of 'Stokes Purple' and 114% the TMY of 'Covington'. 'NCPUR13-0315' had a higher percentage of No.1 roots, the most valuable class, and fewer jumbos and culls (62% No.1, 21% canner, 11% jumbo, and 6% culls) compared to 'Stokes Purple' (51% No.1, 16% canner, 19% jumbo and 14% culls). Thus, for 'NCPUR13-0315', the value per ton harvested is higher, in addition to the higher tonnage per acre, as compared to 'Stokes Purple'.

TABLE 3

'NCP13-0315' average yield and standard deviation and comparison to 'NC413' ('Stokes Purple') and 'Covington' in 9 replicated yield trials in 2016-2019.

| Trial | Total yield bu/A | Marketable yield bu/A | % Marketable yield % 'NC413' | % Marketable yield % 'Covington' |
|---|---|---|---|---|
| 2016 Clinton Purple TS | 1080 ± 106 | 998 ± 68 | 181 ± 64 | 130 ± 27 |
| 2016 Kinston Purple TS | 858 ± 41 | 843 ± 41 | 221 ± 75 | 114 ± 8 |
| 2017 Clinton Purple TS | 523 ± 49 | 513 ± 58 | 136 ± 21 | |
| 2017 Kinston Purple TS | 535 ± 105 | 519 ± 109 | 152 ± 46 | 124 ± 34 |
| 2017 Scott Purple TS | 472 ± 120 | 446 ± 106 | 168 ± 110 | 110 ± 13 |
| 2018 Kinston Purple TS | 416 ± 44 | 416 ± 44 | 205 ± 38 | 156 ± 24 |

TABLE 3-continued

'NCP13-0315' average yield and standard deviation and comparison to 'NC413' ('Stokes Purple') and 'Covington' in 9 replicated yield trials in 2016-2019.

| | | | | |
|---|---|---|---|---|
| 2019 Kinston NCG | 515 ± 147 | 478 ± 128 | NA | 91 ± 25 |
| 2019 Kinston Purple TS | 356 ± 104 | 317 ± 95 | 318 ± 110 | 109 ± 40 |
| 2019 Clinton Purple TS | 503 ± 74 | 474 ± 73 | 129 ± 46 | 83 ± 14 |
| Average | 584 | 556 | 189 | 114 |

| Trial | % No. 1's | % Canner's | % Jumbo's | % Culls |
|---|---|---|---|---|
| 2016 Clinton Purple TS | 61 ± 7 | 18 ± 5 | 14 ± 5 | 7 ± 5 |
| 2016 Kinston Purple TS | 65 ± 5 | 24 ± 6 | 10 ± 4 | 2 ± 0 |
| 2017 Clinton Purple TS | 67 ± 5 | 13 ± 2 | 17 ± 8 | 2 ± 2 |
| 2017 Kinston Purple TS | 76 ± 6 | 13 ± 5 | 8 ± 6 | 3 ± 4 |
| 2017 Scott Purple TS | 62 ± 14 | 14 ± 9 | 19 ± 19 | 5 ± 4 |
| 2018 Kinston Purple TS | 74 ± 13 | 20 ± 11 | 6 ± 8 | 0 |
| 2019 Kinston NCG | 51 ± 6 | 30 ± 7 | 9 ± 5 | 10 ± 5 |
| 2019 Kinston Purple TS | 44 ± 8 | 30 ± 5 | 12 ± 6 | 14 ± 5 |
| 2019 Clinton Purple TS | 57 ± 7 | 28 ± 7 | 8 ± 4 | 7 ± 1 |
| Average | 62 | 21 | 11 | 6 |

*50 lb bushels per acre

Size grading uses the definitions of the National Sweetpotato Collaborators Group:

US # 1's - Roots 2" to 3½" diameter, length of 3" to 9" , must be well shaped and free of defects.

Canners - Roots 1" to 2" diameter. 2" in length.

Jumbo's - Roots that exceed the diameter, length and weight requirements of the above 2 grades, but are of marketable quality Total Marketable Yield - Sum of US #1. Canners and Jumbo's.

Culls - Roots >1" in diameter and so misshapen or unattractive that they could not fit as marketable roots in any of the above Percent US #1's - Calculated by dividing the weight of US #1's by the Total Marketable Yield weight.

Disease or pest resistance: The results of disease evaluations for 'NCPUR13-0315' are summarized in Table 4. Based on multiyear disease evaluations, 'NCPUR13-0315' is moderately resistant to *Fusarium* wilt (*Fusarium oxysporum* Schlect. f. sp. *batatas* (Wollenw.) Snyd. & Hans.), susceptible to *Streptomyces* soil rot (*Streptomyces ipomoeae* (Person & W. J. Martin) Waksman & Henrici) and to southern root knot nematode, *Meloidogyne incognita* (Kofoid & White).

TABLE 4

Disease screen results for 'NCPUR13-0315' by year over four years for Southern root-knot nematode (*Meloidogyne incognita*) (Kofoid & White) (SRKN), fusarium wilt (*Fusarium oxysporum* Schlect. f sp.batatas (Wollenw.) Snyd. & Hans.) (FW), and Streptomyces soil rot (*Streptomyces ipomoeae* (Person & W. J. Martin) Waksman & Henrici) (Field SSR).

| Year | SRKN | FW | Field SSR |
|---|---|---|---|
| 2019 | — | R | — |
| 2018 | MS | R | — |
| 2017 | S | MR | S |
| 2016 | — | MS | — |
| Long term average resistance ratings for select check clones | | | |
| 'NCPUR06-0020' | MS | MR | S |
| 'Stokes Purple' | R | MR | S |

TABLE 4-continued

Disease screen results for 'NCPUR13-0315' by year over four years for Southern root-knot nematode (*Meloidogyne incognita*) (Kofoid & White) (SRKN), fusarium wilt (*Fusarium oxysporum* Schlect. f sp.batatas (Wollenw.) Snyd. & Hans.) (FW), and Streptomyces soil rot (*Streptomyces ipomoeae* (Person & W. J. Martin) Waksman & Henrici) (Field SSR).

| | | | |
|---|---|---|---|
| 'Covington' | R | R | R |

Scale - HS — highly susceptible, S — susceptible, MS — moderately susceptible, MR — moderately resistant, R resistant, HR — highly resistant.

The root knot nematode rating is based on the number of galls on roots counted eight weeks after inoculation with 10,000 eggs of M. incognita race 3 in plants established in four-inch pots. Gall count classes: HR = 0; R = 1-3; MR = 4-10; MS = 11-30; S = 31-100; HS = 101 + galls. 4 reps.

The Fusarium wilt rating involves dipping fresh cut plants in a solution of Fusarium oxysporum spores then rating for mortality and vascular tissue browning. 3 reps of five plants each are used.

Streptomyces soil rot is screened in a field trial with high levels of SSR pressure. Plots are rated for fibrous root damage, yield and storage root lesions.

Long term storage: Sweetpotatoes from yield trials are stored and rated for the ability to last until the next crop season. They are rated on a visual pithiness scale from 0 to 4, where 0 has visible holes, to 4, where there is no visible pithiness, or they look like freshly harvested roots. This rating system is used as an estimate of how well the roots have lasted in storage. The sweetpotatoes are also rated for sprouting, another measure of long-term storage, which is also reflected in the pithiness score. 'NCPUR13-0315' had an average score of 1.8 on the pithiness scale over 5 trials from 2014 to 2019 (Table 5). In the same years, 'Covington' averaged 2.4, 'Stokes Purple' averaged 2.4, and 'NCPUR06-0020' averaged 2.8 on the pithiness scale, which are all considered good for storage ability. Thus, the storage ability of 'NCPUR13-0315' can be considered to be fair. Sprouting in storage was minimal for 'NCPUR13-0315'.

TABLE 5

Pithiness rating as an estimate of long-term storage of 'NCPUR13-0315' compared to check lines 2014-2019.

| Clone | Pithiness | # Ratings |
|---|---|---|
| 'NCPUR13-0315' | 1.8 ± .8 | 5 |
| 'NCPUR06-0020' | 2.8 ± 0.6 | 36 |
| 'Covington' | 2.4 ± 0.4 | 185 |
| 'Stokes Purple' | 2.4 ± 0.6 | 31 |

Pithiness rating: six storage roots cut and rated in August of the year after harvest. Mean ± std dev Scale: 0 = large holes; 1 = holes, light areas; 2 = no holes, some light areas; 3 = slightly pithy; 4 = no pithiness.

Flood tolerance: The flood tolerance of 'NCPUR13-0315', observed under wet conditions, appears to be significantly less than 'Covington'. 'Covington' is considered tolerant to wet conditions, though any cultivar will be lost if submerged. 'NCPUR13-0315' will show a proliferation of lenticels under wet conditions.

We claim:

1. A new and distinct cultivar of *Ipomoea batatas* plant named 'NCPUR13-0315', substantially as illustrated and described herein.

* * * * *